United States Patent [19]

Inaoka et al.

[11] Patent Number: 4,804,676
[45] Date of Patent: Feb. 14, 1989

[54] ENKEPHALINASE B INHIBITORS, THEIR PREPARATION, AND PHARMACEUTICAL COMPOSITIONS CONTAINING THE SAME

[75] Inventors: Yoshinori Inaoka; Shuji Takahashi; Hidetsune Tamaoki; Ryuzo Enokita, all of Hiromachi, Japan

[73] Assignee: Sankyo Company Limited, Tokyo, Japan

[21] Appl. No.: 782,524

[22] Filed: Oct. 1, 1985

[30] Foreign Application Priority Data

Oct. 4, 1984 [JP] Japan .................................. 59-208789

[51] Int. Cl.⁴ ..................... A61K 31/40; C07D 207/09
[52] U.S. Cl. .................................... 514/423; 548/537; 435/121
[58] Field of Search ......................... 548/537; 514/423

[56] References Cited

U.S. PATENT DOCUMENTS 4,284,561  8/1981  Petrillo, Jr. et al. ............ 548/537 X
4,663,342  5/1987  Umezawa et al. .................. 514/423

FOREIGN PATENT DOCUMENTS 0167936  1/1986  European Pat. Off. ............ 514/423
0097266  8/1981  Japan ................................. 514/423

*Primary Examiner*—Joseph Paul Brust
*Attorney, Agent, or Firm*—Frishauf, Holtz, Goodman & Woodward

[57] ABSTRACT

Propioxatins A and B, which have the formula:

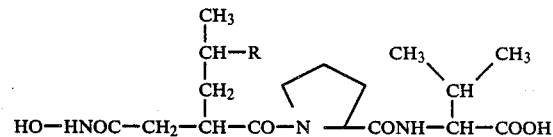

wherein R represents a hydrogen atom or a methyl group, can be prepared by cultivating a suitable strain of Kitasatosporia, e.g. Kitasatosporia sp. SANK 60684 (FERM-P 7581). They can be salified to give pharmaceutically acceptable salts. The compounds are active as enkephalinase B inhibitors and are thus capable of enhancing enkephalin activity in vivo.

4 Claims, 4 Drawing Sheets

ENKEPHALINASE B INHIBITORS, THEIR PREPARATION, AND PHARMACEUTICAL COMPOSITIONS CONTAINING THE SAME

BACKGROUND OF THE INVENTION

The present invention relates to novel enkephalinase B inhibitors.

Following the discovering of morphine receptors in vivo, a search was made for endogenous morphine-like substances, and the pentapeptides methionine-enkephalin (Tyr-Gly-Gly-Phe-Met) and leucine-enkephalin (Tyr-Gly-Gly-Phe-Leu) were found in mammalian brain by Hughes et al. (Nature, 258, 577 (1975)). Various other endogenous opioid peptides were subsequently found and it became apparent that these other peptides necessarily have a methionine-enkephalin or leucine-enkephalin structure at their N-terminal region.

Enkephalins (Met-enkephalin and Leu-enkephalin) are generally short-lived in vivo, being rapidly degraded into active derivatives, so their potential value as pharmaceuticals is limited because their analgesic function cannot last long after administration. If suitable enzyme inhibitors could be found to suppress the degradation of enkephalins in vivo, their biological activity could be maintained, making them potentially useful as analgesics.

The degradation system in the brain includes aminopeptides which exist in the soluble fraction and the brain membrane, as well as enkephalinase A, enkephalinase B and angiotensin-converting enzymes which exist in the membrane. Aminopeptidases cleave the Tyr-Gly bond of enkephalins and release Tyr, whereas enkephalinase A and angiotensin-converting enzymes cleave the Gly-Phe bond and release Tyr-Gly-Gly. Aminopeptidase inhibitors are known, such as puromycin (Proc. Natl. Acad. Sci., U.S.A. 69, 624 (1972)), bestatin (J. Antibiotics, 29, 97 (1976)), amastatin (J. Antibiotics, 31, 636 (1978)) and alphamenine (J. Antibiotics, 36, 1572, 1576 (1983)). Enkephalinase A inhibitors are also known, such as thiorphan (Nature, 288, 286 (1980)) and phosphoramidon (Life Science, 29, 2593 (1981)). Enkephalinase A inhibitors are also described in French patent specification Nos. 2 480 747 and 2 518 088 (corresponding to Japanese laid-open patent application "kokai" No. 58-150547).

On the other hand, to the best of our present knowledge, the action of enkephalinase B has not previously been investigated in detail, and no effective inhibitors for it have been described hitherto.

BRIEF SUMMARY OF THE INVENTION

We have purified enkephalinase B from rat brain membrane and investigated its properties, establishing that the enzyme hydrolyzes specifically only enkephalins, and not enkephalin-related peptides and other biologically active peptides. This indicates that enkephalinase B mainly takes part in enkephalin metabolism. We have also established that enkephalinase B differs from the other enzymes mentioned above, in that it cleaves the Gly-Gly bond of enkephalins to release Tyr-Gly.

Following on from this, we have now discovered new compounds (hereinafter referred to as Propioxatins A and B) which specifically inhibit enkephalinase B and can be produced by cultivation of a microorganism of the genus Kitasatosporia, strain SANK 60684 (FERM-P 7581).

The enkephalinase A inhibitors of the above-mentioned French patent specification Nos. 2 480 747 and 2 518 088, like those of the present invention, are oligopeptides; but they differ in their amino-acid structure and they are produced synthetically rather than by microbial culture. Example 3 given below shows the differences in activity between the compounds of the present invention and a representative compound of French specification No. 2 518 088.

Accordingly, it is an object of this invention to provide, as new compositions of matter, the compounds Propioxatins A and B and pharmaceutically acceptable salts thereof.

It is a further object of the invention to provide pharmaceutically active compositions having enkephalinase B inhibitory activity and comprising at least one of the said new compounds or salts.

It is a yet further object of the invention to provide a process for the preparation of the said new compounds by isolation from a culture of a suitable microorganism of the genus Kitasatosporia.

DETAILED DESCRIPTION OF THE INVENTION

Figure 1:
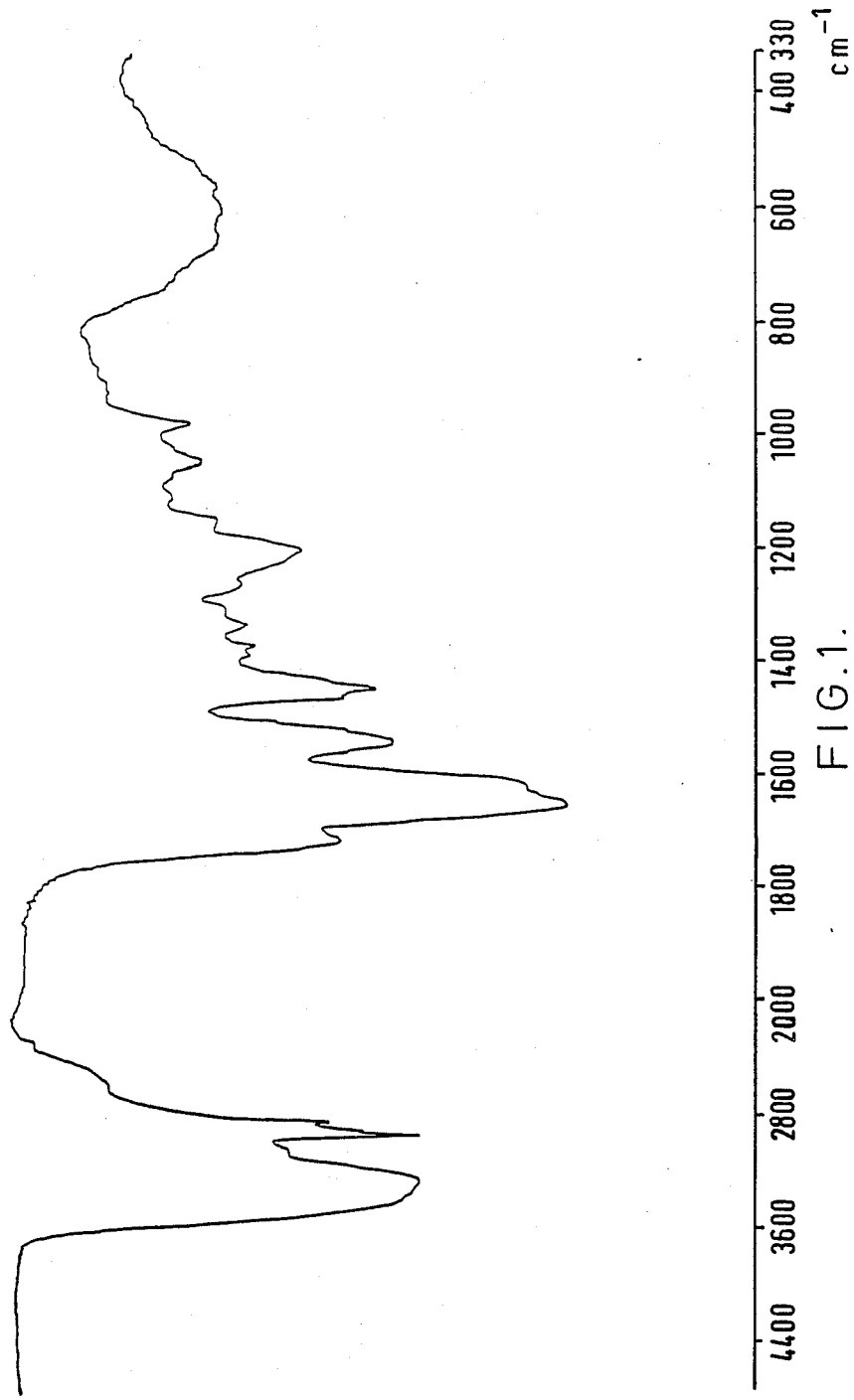
FIG. 1 shows the infrared absorption spectrum of Propioxatin A.

Propioxatins A and B having the following formula:

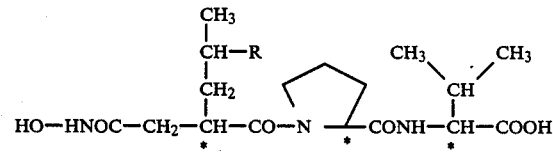

wherein R is a hydrogen atom in Propioxatin A, and R is a methyl group in Propioxatin B. The molecule contains three asymmetric carbon atoms at the positions indicated by the asterisks in the above formula, and we believe that these respectively have the (R), (S) and (S) configurations (reading from left to right) in the products as obtained by cultivation of the above-mentioned microorganism.

Kitasatosporia strain SANK 60684 used in the present invention has the following mycological properties.

(1) Morphological properties

Strain SANK 60684 exhibits relatively good growth when cultured for identification on an agar medium at 28° C. for 7 to 14 days, and its substrate mycelium elongates and branches abundantly. The width of substrate mycelium is 0.5 to 0.8 μm and neither plasmotomy nor Nocardia-like zigzag elongation is observed. The aerial mycelium is 0.5 to 0.8 μm wide, and possesses the morphological properties shown in Table 1. Sporophores adhere on the aerial mycelium only. No special organs are observed, such as sporangia, flagellar spores, sclerotia or trochoid branches.

TABLE I

Morphological properties of aerial mycelium of SANK 60684

| | |
|---|---|
| Branching of mycelium: | simple |
| Form of sporophore: | straight or curved |
| Surface structure of spore: | smooth |
| Size of spore: | 0.6 to 0.9 × 1.4 to 2.2 μm |
| Shape of spore: | elliptic or columnar |
| Number of linked spores: | 10 to 50 |

(2) Properties on various media

Appearance and properties on various plate media when cultured at 28° C. for 14 days are shown in Table 2. Color tones are indicated according to the color chip numbers of the "Standard Color Chips" issued by Nippon Shikisai Kenkyusho. The key to the abbreviations used follows the end of the table.

TABLE 2

Appearance and properties of cultures on various media

| | | |
|---|---|---|
| Sucrose-nitrate agar | G | barely good; flat; pale yellowish orange (2-9-9) |
| | AM | slightly formed; white |
| | R | pale yellowish orange (2-9-9) |
| | SP | not produced |
| Glucose-asparagine agar | G | good; flat; brownish white (2-9-8) |
| | AM | abundantly formed; velvety; pale yellowish brown (3-7-8) |
| | R | pale yellowish brown (3-7-8) |
| | SP | not produced |
| Glycerol-asparagine agar (ISP5) | G | very good; flat; brownish white (1-9-6) |
| | AM | abundantly formed; velvety; brownish white (1-8-6) |
| | R | pale yellowish brown (3-7-8) |
| | SP | not produced |
| Starch-inorganic salt agar (ISP4) | G | good; flat; pale yellowish brown (4-8-9) |
| | AM | barely good; brownish white (1-8-6) |
| | R | grayish yellow brown (3-6-8) |
| | SP | not produced |
| Tyrosine agar (ISP7) | G | very good; flat; pale yellowish orange (2-9-9) |
| | AM | abundantly formed; velvety; brownish white (1-9-6) |
| | R | pale yellowish brown (4-8-8) |
| | SP | not produced |
| Peptone-yeast extract-iron agar (ISP6) | G | good; flat; pale yellowish orange (2-9-9) |
| | AM | not formed |
| | R | pale yellowish brown (4-8-9) |
| | SP | not produced |
| Nutrient agar (Difco) | G | good; flat; pale yellowish orange (2-9-9) |
| | AM | not formed |
| | R | pale yellowish brown (4-8-9) |
| | SP | not produced |
| Yeast-malt agar (ISP2) | G | very good; flat or elevated; pale brown (2-8-9) |
| | AM | abundantly formed; velvety; brownish white (1-8-6) |
| | R | pale yellowish brown (6-7-9) |
| | SP | not produced |
| Oatmeal agar (ISP3) | G | very good; flat; bright brownish gray (2-7-8) |
| | AM | abundantly formed; velvety; brownish white (1-8-6) |
| | R | pale yellowish brown (4-7-8) |
| | SP | pale yellowish brown (weak, 3-7-8) |
| Water agar | G | barely good; flat; brownish white (1-9-6) |
| | AM | barely good; velvety; brownish white (1-9-6) |
| | R | brownish white (1-9-6) |
| | SP | not produced |
| Potato extract-carrot extract agar | G | excellent; flat; pale yellowish orange (2-9-9) |
| | AM | abundantly formed; velvety; brownish white (1-8-6) |
| | R | brownish white (1-8-6) |
| | SP | not produced |

(3) Physiological properties (1) Temperature range for growth (yeast-malt agar, ISP2 medium, 2 weeks): 6° C. to 38° C. Most suitable temperature for growth: 17° C. to 28° C.

(2) Liquefaction of gelatin: Negative (glucose-peptone-gelatin medium, stab culture)

Hydrolysis of starch: Positive (starch-inorganic salt agar ISP4 medium, iodine reaction)

Coagulation and peptonization of skim milk: Positive (skim milk produced by Difco Co. Ltd.)

Nitrate reduction: Positive (3) Formation of melanine-like pigment (28° C., 2 weeks):

Tyrosine agar medium (ISP7): Negative

Peptone-yeast extract-iron agar medium (ISP6): Negative

Triptone-yeast extract broth (ISP1): Negative (4) Decomposition

Tyrosine: Negative

Xanthine: Negative

Casein: Positive (5) Salt resistance (yeast-malt agar ISP2 medium, 2 weeks):

Capable of growing on a medium containing 2% of salt, but incapable of growing on a medium containing 3% or more of salt (6) Utilization of carbon sources The following results have been obtained after cultivation on a Pridham-Gottlieb agar as a basic medium at 28° C. for 14 days:

D-glucose can be utilized, but utilization of D-xylose is doubtful. L-arabinose, inositol, D-mannitol, D-fructose, L-rhamnose, sucrose and raffinose cannot be utilized.

(4) Histochemical properties

A mesodiaminopimelic acid, LL-diaminopimelic acid, and glycine have been detected in the hydrolyzate of the whole cells (Appl. Microbiol., 13, 236, 1965). Glucose, galactose and mannose were detected as sugar components.

From the above results the strain SANK 60684 has been assigned to the genus Kitasatosporia and has been designated Kitasatosporia sp. SANK 60684. The strain was deposited on Apr. 11, 1984 with the Fermentation Research Institute, Agency of Industrial Science and Technology, Ministry of Industrial Trade and Industry, Japan, under the accession number FERM-P 7581.

Although the preparation of the Propioxatins in accordance with the present invention is described herein with particular reference to strain SANK 60684, it is well known that various properties of actinomycetes are not fixed, but may be easily varied naturally and artificially. Accordingly, other Propioxatin-producing strains of the genus Kitasatosporia may also be used in the process of the invention.

The cultivation of the Propioxatin-producing microorganisms in the process of the present invention may be carried out according to the methods conventionally employed for actinomycetes. Shaken culture or submerged culture in a liquid nutrient medium is preferred. The medium employed may contain any of the well-known assimilable nutrient sources for actinomycetes, including at least one carbon source, one nitrogen source and inorganic salts. For instance, glucose, sucrose, glycerol, maltose, dextrin, starch, soybean oil or cottonseed oil may be used as a carbon source; soybean meal, peanut meal, cottonseed meal, fermamine fish meal, corn steep liquor, peptone, meat extract, yeast, yeast extract, sodium nitrate, ammonium nitrate, ammonium sulfate or various amino acids may be used as a nitrogen source; and sodium chloride, phosphates, calcium carbonate and trace metal salts may be used as inorganic salts. In carrying out cultivation in a liquid medium an antifoaming agent may be suitably employed such as silicone oil, a vegetable oil, or a surfactant. The pH of the medium may be from 5.5 to 8.0 and the cultivation temperature from 6° to 38° C., preferably about 28° C.

Isolation and purification of the Propioxatins from the microbial culture can be achieved by per se conventional techniques. Thus, after removing the mycelium (e.g. by filtration or centrifugation), the Propioxatins can be isolated from the culture broth filtrate in a good yield by adsorption onto an adsorbent material and then eluting them therefrom. For example, the adsorbent may be Diaion HP20 (produced by Mitsubishi Chemical Industries Ltd.) and most of the Propioxatins adsorbed thereon can be eluted by 50% aqueous ethanol. Alternatively, they can be isolated from the filtrate by solvent extraction. The Propioxatins may be extracted into an n-butanol layer at pH 2.0 and re-extracted into an aqueous layer at pH 7.0. Ion exchange chromatography may also be used for purification of the compounds and an ion exchanger having diethylaminoethyl groups (DEAE) is particularly effective. For example, the Propioxatins may be adsorbed by DEAE-Sephadex (produced by Pharmacia Co. Ltd.) or DEAE-Toyopearl 650S (produced by Toyo Soda K.K.) and then eluted therefrom by using increasing concentrations of acetic acid. A reverse phase silica gel column may be also employed and an ODS (octadecyl group) column for high pressure chromatography can separate Propioxatin A and Propioxatin B from each other extremely effectively. Propioxatins A and B can be obtained as pure white powders by applying the above-mentioned methods in a suitable combination.

The presence of the desired substances, Propioxatins A and B, can be assessed quantitavely during the processes of cultivation and purification by measuring the enkephalinase B inhibition activity. To do this, methionine-enkephalin is incubated with an enkephalinase B solution containing the Propioxatin, and then the amount of the resulting product tyrosyl-glycine (Tyr-Gly) is estimated by chromatography (e.g. thin layer chromatography or high pressure liquid chromatography). A blank test without Propioxatin is also carried out, and the enkephalinase B inhibition constant is determined. The enkephalinase B solution used for this technique can be prepared from rat brain by generally-known enzyme purification methods. Since enkephalinase B exists in rat brain as a membrane-bound enzyme, it is released from the membrane and made soluble using a detergent such as Triton X-100. The solubilized enzyme is then subjected to a combination of purification processes such as ion-exchange chromatography in which various kinds of ion-exchangers having a diethylaminoethyl (DEAE) group can be used, gel filtration using a molecular sieve, or isoelectric fractionation to obtain the purified enkephalinase B. These methods are described in greater detail hereinafter in the Examples.

The thus obtained Propioxatins A and B, respectively, have the following physicochemical and biological properties.

Figure 2:
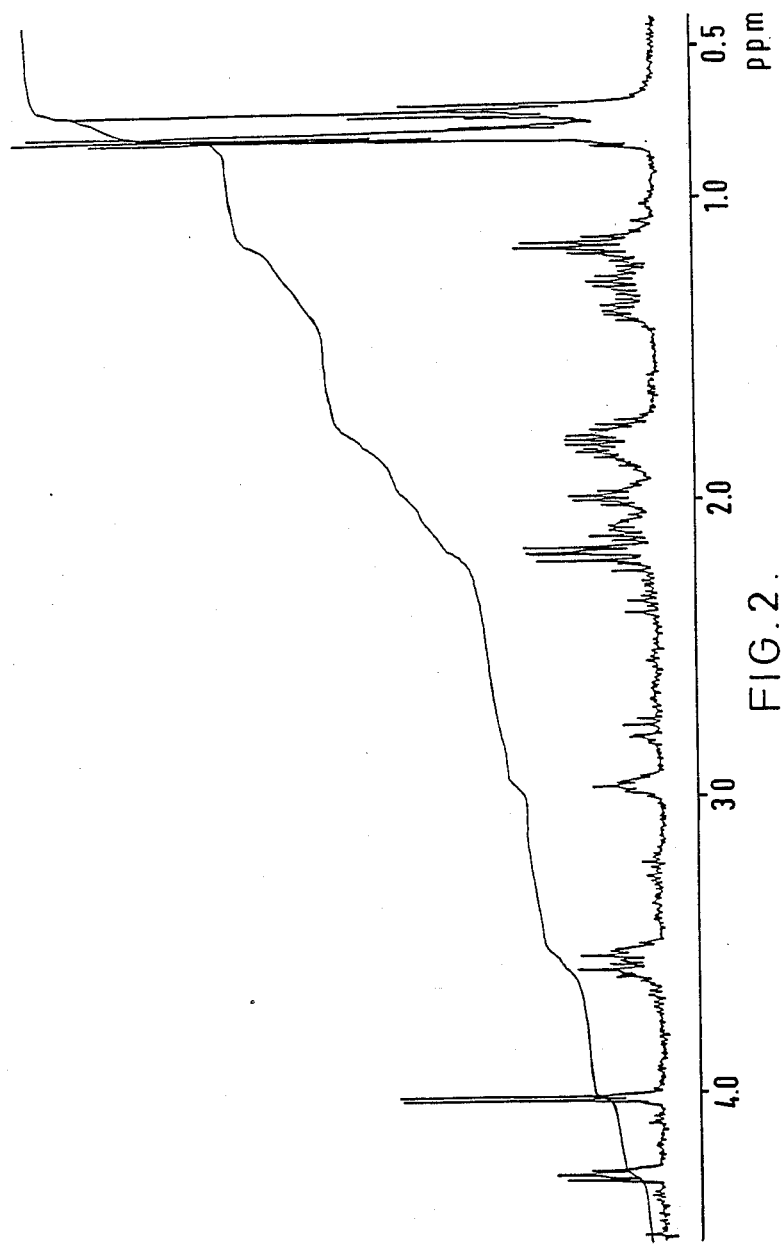
FIG. 2 shows the nuclear magnetic resonance spectrum of Propioxatin A.

1. Physicochemical and biological properties of Propioxatin A
   (1) White acidic powder
   (2) Elementary analysis (%): C, 54.67; H, 7.51; N, 11.67
   (3) Molecular weight: 371 (measured by mass spectrometry)
   (4) Molecular formula: $C_{17}H_{29}N_3O_6$
   (5) Specific rotation:
   $[\alpha]_D^{25} = -70.9°$ (C=1.0, water)
   (6) IR absorption spectrum ($\nu_{max}^{KBr}$ cm$^{-1}$):
   The IR absorption spectrum measured using a KBr tablet is as shown in FIG. 1 of the drawings.
   (7) NMR spectrum (δ ppm):
   The 400 MHz NMR spectrum measured in heavy water using tetramethylsilane as external standard is as shown in FIG. 2 of the drawings.
   (8) UV spectrum {$\lambda_{max}$ nm ($E_{1\,cm}^{1\%}$)}
   The UV spectrum measured in an aqueous solution does not show any characteristic absorptions other than the absorption at the terminal region.
   (9) Solubility: Soluble in water, methanol and dimethyl sulfoxide; slightly soluble in ethanol and acetone; and insoluble in ethyl acetate, chloroform, benzene and ether.
   (10) Acid hydrolysis: Yields one molecule each of valine and proline. (Detected with an automatic amino acid analyzer after hydrolysis with 12N hydrochloric acid-glacial acetic acid (1:1) at 110° C. for 24 hours).
   (11) Color reaction: Negative ninhydrin reaction. Positive ninhydrin reaction after hydrolysis.
   (12) Elution time by high pressure liquid chromatography: Propioxatin A was eluted at about 6.5 minutes on a TSK-GEL, ODS 120A column (0.46×25 cm, produced by Toyo Soda Kogyo) using an aqueous solution containing 20% acetonitrile-0.1% trifluoroacetic acid at a flow rate of 1.0 ml/minute. It was detected by monitoring UV absorption at 230 nm.
   (13) Inhibition of enkephalinase B: Propioxatin A is a competitive inhibitor and the Ki value (inhibition constant) is $1.3 \times 10^{-8}$M.

Figure 3:
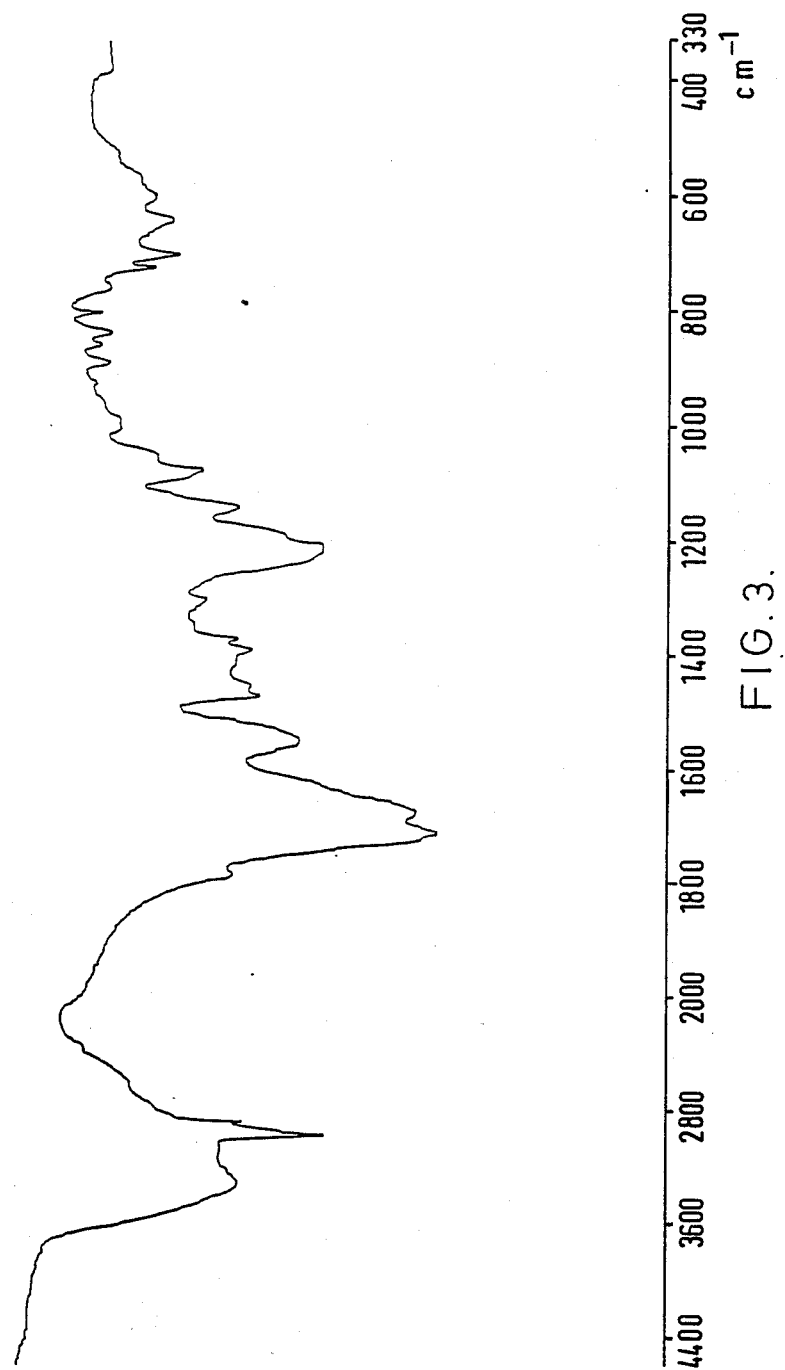
FIG. 3 shows the infrared absorption spectrum of Propioxatin B.

2. Physicochemical and biological properties of Propioxatin B
   (1) White acidic powder
   (2) Elementary analysis (%): C, 50.59; H, 7.19; N, 9.59
   (3) Molecular weight: 385 (measured by mass spectrometry)
   (4) Molecular formula: $C_{18}H_{31}N_3O_6$
   (5) Specific optical rotation:
   $[\alpha]_D^{25} = -51.3°$ (C=1.0, water)
   (6) IR absorption spectrum ($\nu_{max}^{KBr}$ cm$^{-1}$).
   The IR absorption spectrum measured using a KBr tablet is as shown in FIG. 3 of the drawings.
   (7) NMR spectrum (δ ppm)

Figure 4:
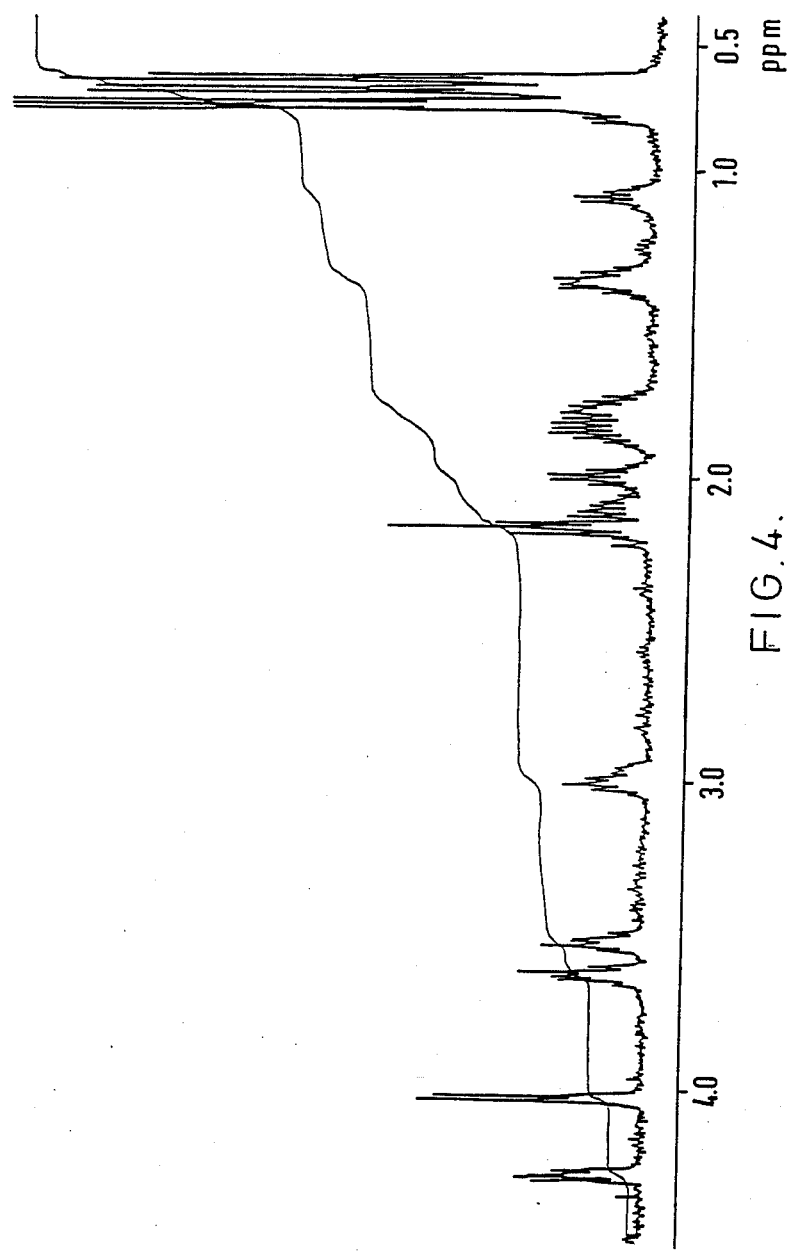
FIG. 4 shows the nuclear magnetic resonance spectrum lof Propioxatin B.

The 400 MHz NMR spectrum measured in heavy water using tetramethylsilane as external standard is as shown in FIG. 4 of the drawings.

(8) UV spectrum $\{\lambda_{max}\text{nm} (E_{1\ cm}^{1\%})\}$

The UV spectrum measured in an aqueous solution does not show any characteristic absorptions other than the absorption at the terminal region.

(9) Solubility:

Soluble in water, methanol and dimethyl sulfoxide; slightly soluble in ethanol and acetone; and insoluble in ethyl acetate, chloroform, benzene and ether.

(10) Acid hydrolysis:

Yields one molecule each of valine and proline. (Detected with an automatic amino acid analyzer after hydrolysis with 12N hydrochloric acid-glacial acetic acid (1:1) at 110° C. for 24 hours).

(11) Color reaction:

Negative ninhydrin reaction. Positive ninhydrin reaction after hydrolysis.

(12) Elution time by high pressure liquid chromatography: Propioxatin B was eluted at about 12.1 minutes on a TSK-GEL, ODS 120A column (0.46×25 cm, produced by Toyo Soda Kogyo) using an aqueous solution containing 20% acetonitrile-0.1% trifluoroacetic acid at a flow rate of 1.0 ml/minute. It was detected by monitoring UV absorption at 230 nm.

(13) Inhibition of enkephalinase B:

Propioxatin B is a competitive inhibitor and the Ki value (inhibition constant) is $1.1 \times 10^{-7}$M.

Salts of the Propioxatins can be prepared in the conventional manner by reaction in solution with a salt of a pharmaceutically acceptable cation. The sodium, potassium, magnesium and calcium salts are preferred.

Pharmaceutical compositions can be prepared by formulating at least one Propioxatin or pharmaceutically acceptable salt thereof with a pharmaceutically acceptable carrier by conventional techniques. Thus, suitable types of formulation for the compounds of the present invention include those for parenteral administration by means of hypodermic, intravenous or intramuscular injection, suppositories, and those intended for oral administration, e.g. tablets, coated tablets, granules, powders and capsules. Pharmaceutical adjuvants appropriate to the type of formulation may also be included, as is conventional in the pharmaceutical art. For instance, when an injection is prepared, a pH adjusting agent, a buffer or a stabilizer can be added to the Propioxatin or a salt thereof, and the whole lyophilized by conventional methods to make a lyophilized injection. When an oral solid preparation is prepared, an excipient, a binder, a disintegrating agent, a lubricant, a coloring agent, a flavor-improving agent, or an odor-improving agent can be added to the compound used as the active ingredient, and then the whole formed into tablets, coated tablets, granules, powders or capsules by conventional methods. When a rectal suppository is prepared, an excipient and optionally a surfactant can be added to the active ingredient, and then the whole formed into suppositories by conventional methods.

The optimum dosage of Propioxatin or salt thereof to be administered will vary with such factors as the age and condition of the patient. However, in the case of adults, the normal oral or parenteral dose will generally be in the range of from 0.01 to 100 mg of Propioxatin or salt thereof, administered from once to three times a day.

The preparation and activity of the compounds of the invention, as well as the methods used for quantitative determination of enkephalinase B inhibitor activity, are illustrated by the following non-limiting Examples.

EXAMPLE 1

Preparation of Propioxatins A and B

Two 2-liter Erlenmeyer flasks, each containing one liter of nutrient medium, were inoculated with spores of Kitasatosporia sp. SANK 60684 (FERM-P 7581). The nutrient medium was at pH 6.85 and contained 3.0% of glucose, 1.0% of live yeast, 3.0% of delipidized soybean meal, 0.4% of calcium carbonate, 0.2% of magnesium chloride and 0.005% of antifoaming agent (Disfoam CB-422, produced by Nihon Yushi K.K.). The flasks were subjected to shaken culture for 4 days at 28° C. and 150 strokes per minute.

The contents of each flask were then poured into each of two 30-liter jar fermentors containing 15 liters of the same nutrient medium and cultured therein for 4 days at 28° C. with stirring. The culture broth was filtered with Celite to remove the mycelium, and 28 liters of filtrate were obtained.

The filtrate was applied to a column containing 20% by volume of Diaion HP 20 adsorbtion resin and the Propioxatins adsorbed thereon were eluted using 50% aqueous ethanol. The ethanol eluate was condensed under reduced pressure to approximately 2 liters. The pH of the solution was adjusted to 2.0 with hydrochloric acid and the solution was extracted with an equal volume of n-butanol, to extract almost all of the Propioxatins into the n-butanol layer. The pH of the n-butanol layer was adjusted to 7.0 using a sodium hydroxide solution, followed by extraction with water, and the Propioxatins now passed into the aqueous layer.

The aqueous layer was applied to a column (4.5×35 cm) of DEAE-Sephadex A-25 (acetic acid type, produced by Pharmacia Co. Ltd.) to allow the Propioxatins to be adsorbed. Elution was carried out by the linear concentration gradient method, using from 10 mM acetic acid (2.5 liters) to 1M acetic acid (2.5 liters). The eluate was fractionated by means of a fraction collector into 20 ml fractions, to obtain the fractions containing Propioxatins. The fractions were lyophilized in vacuo to give approximately 700 mg of crude powder.

This crude powder was dissolved in 50 ml of 10 mM acetic acid and was allowed to be adsorbed on a column (2.2×28 cm) of DEAE-Toyopearl 650S (acetic acid type, produced by Toyo Soda Kogyo K.K.). Elution was carried out by the linear concentration gradient method, using from 10 mM acetic acid (0.5 liter) to 1M acetic acid (0.5 liter), and the eluate was fractionated by means of a fraction collector into 10 ml fractions, to obtain the fractions containing Propioxatins. The fractions were lyophilized in vacuo to give 300 mg of crude powder. The crude powder was dissolved in 0.5 ml of acetonitrile/water (15:85) containing 0.1% trifluoroacetic acid and the solution was applied to a reverse phase silica gel column (TSK-GEL ODS-120A, 0.78×30 cm, produced by Toyo Soda Kogyo K.K.). Elution was carried out at a flow rate of 2.0 ml/minute using the same mixture as in the foregoing procedure, eluting Propioxatin A in about 20 minutes, and Propioxatin B in about 48 minutes. Both of the substances were concentrated under reduced pressure, dissolved in a small amount of water, and lyophilized in vacuo to give 14 mg of Propioxatin A and 4 mg of Propioxatin B, respectively, as pure white powders.

EXAMPLE 2

Preparation of Enkephalinase B Enzyme Solution 100 g of rat brain was homogenized using 1 liter of 50 mM tris-HCl buffer (pH 7.7) and the homogenate was centrifuged at 50,000 G for 15 minutes to give a precipitate. The precipitate was washed three times and centrifuged as before. It was then suspended in 500 ml of the same buffer containing 1% of Triton X-100, and kept at 37° C. for 1 hour. The suspension was centrifuged at 100,000 G for 1 hour to give a crude enzyme solution of enkephalinase B as supernatant.

The thus obtained crude enzyme solution was dialyzed against a 5 mM sodium phosphate buffer (pH 7.0) and was applied for adsorption to a column (3.0×30 cm) of DEAE-Sephacel (produced by Pharmacia Co. Ltd.) previously equilibrated with the same buffer containing 1% Triton X-100 (solution A). The column was washed with solution A and eluted with 2.5 liters of solution A and with 2.5 liters of solution A which contains 0.4M sodium chloride by the linear concentration gradient method.

The obtained fraction of enkephalinase B was dialyzed against solution A, and was applied for adsorption to a column (1.6×27 cm) of DEAE-Toyopearl 670S (produced by Toyo Soda Kogyo K.K.) previously equilibrated with solution A. Elution was carried out using 500 ml of solution A and 500 ml of a solution of 0.4M sodium chloride dissolved in solution A by the linear concentration gradient method. The obtained fraction of enkephalinase B was dialyzed against 0.025M imidazole-hydrochloric acid buffer (pH 7.4) and applied for adsorption to a column (1.0×26 cm) of Polybuffer exchanger PBE 94 (produced by Pharmacia Co. Ltd.), previously equilibrated with the same buffer. A solution prepared by diluting Polybuffer 74 (produced by Pharmacia Co. Ltd.) with water to a ninefold dilution, and by adjusting its pH to 4.0 with hydrochloric acid, was applied to the column to give an enkephalinase B fraction.

The fraction of enkephalinase B was concentrated to approximately 1.0 ml with Collodion Pack (produced by MS Kiki K.K.), and the solution was applied to a column (1.6×79 cm) of Toyopearl HW-55 (produced by Toyo Soda Kogyo K.K.) previously equilibrated with a 50 mM sodium phosphate buffer (pH 7.0) containing 0.1M sodium chloride. Gel filtration was carried out by applying the same buffer to the column to give a fraction of enkephalinase B.

The enzymatic properties of the enkephalinase B thus obtained were as follows:

Enzymatic properties of enkephalinase B molecular weight: approximately 80,000
optimum pH: 6.5
isoelectric point: 4.2
Km value relative to Methionine-enkephaline (Michaelis constant): $5.3 \times 10^{-5}$M

EXAMPLE 3

Inhibition of enkephalinase B by Propioxatins A and B

A mixture of 40 μl of 0.1M sodium phosphate buffer (pH 6.5), 10 μl of a Propioxatin A solution and 40 μl an enkephalinase B solution was incubated at 37° C. for 5 minutes, then 10 μl of a 1 mM or 10 mM methionine-enkephalin solution were added, followed by stirring at 37° C. for 20 minutes. The reaction was then stopped by adding 10 μl of 2N hydrochloric acid to the reaction mixture, and the amount of tyrosyl-glycine (Tyr-Gly) produced (Vi) with respect to 20 μl of the reaction mixture was determined by high pressure liquid chromatography. Similarly, the amount of tyrosyl-glycine produced (V) in a blank test, in which no Propioxatin was contained and only a buffer was used, was measured.

The enkephalinase B inhibitor constant (Ki) was calculated by the method of Dixon (Dixon M, Biochem. J., 55, 170 (1953)). The Ki value of Propioxatin A was $1.3 \times 10^{-8}$M.

The determination carried out in the same manner but for Propioxatin B gave a Ki value of $1.1 \times 10^{-7}$M.

The high pressure liquid chromatography performed herein was under the following conditions: eluent, 10 mM potassium phosphate/methanol (1000:50); column, M & S Pack $C_{18}$ (0.46×15 cm, produced by MS Kiki K.K.); and flow rate, 1.0 ml/minute. The determination was carried out with a fluorescence spectromonitor (RF530, produced by Shimazu Seisakusho K.K.) using an excitation wavelength of 275 nm and a fluorescence wavelength of 304 nm, to find that tyrosyl-glycine was eluted approximately 6 minutes after injection of the sample.

By way of comparison, the enkephalinase B inhibition activity was also measured for the compound N-[3-(N-hydroxycarbamoyl)-2-benzylpropanoyl]alanine, which is a compound within formula (I) of the above-mentioned French patent specification No. 2 518 088 (Japanese laid-open application No. 58-150547). The method of Parker and Waud (J. Pharmacol. Exper. Ther. 177, 1, 1971) was used to calculate the concentration of the compound inhibiting 50% of enzyme activity ($IC_{50}$). This method is also used in the French specification, at page 61, to assess the enkephalinase A activity of the compounds mentioned therein. The $IC_{50}$ for enkephalinase B was measured against a substrate of 0.1 mM methionine-enkephalin and the following results obtained:

|  | $IC_{50}$ |
| --- | --- |
| Propioxatin A | 11.1 ng/ml |
| Compound of FR 2 518 088 | 13000 ng/ml |

Thus, Propioxatin A was approximately 1,000 more active than the prior art compound in this test.

EXAMPLE 4

Analgesic effects of Propioxatins

Propioxatin A (10 μg) and enkephalin (1 mg) were administered simultaneously into the cereberal ventricle of a rat and the analgesic action thereof was examined by the Randall-Selitto method (Randall, L. D. and Selitto, J. J.; Arch. Int. Pharmacodyn. 111, 409–419 (1957)). The same quantities of Propioxatinn A and enkephalin were also administered separately, as controls.

It was found that enkephalin alone, and the combination of enkephalin with Propioxatin A, both produced a similar peak value of analgesic effect approximately 10 minutes after injections; but whereas the analgesic effect of the enkephalin alone had fallen to 50% of its peak value after about 30 minutes, it took about 90 minutes for this to happen with the enkephalin/Propioxatin A combination. No appreciable analgesic effect was obtained with Propioxatin A injected alone.

This demonstrates that Propioxatin A is significantly effective in prolonging the analgesic action of enkephalin.

We claim:

1. A compound having the formula:

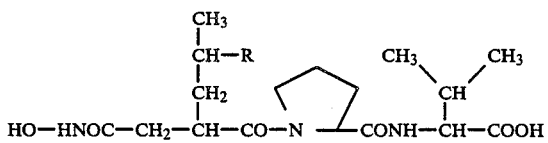

wherein r represents a hydrogen atom or a methyl group, and pharmaceutically acceptable salts thereof.

2. Propioxatin A having the formula:

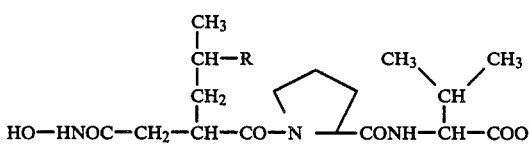

wherein R represents a hydrogen atom.

3. Propioxatin B having the formula:

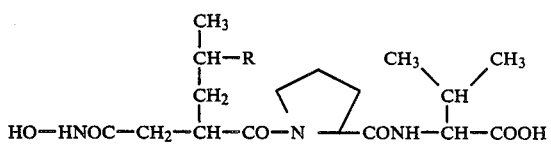

wherein R represents a methyl group.

4. A pharmaceutical composition for use as an enkephalinase B inhibitor comprising an effective amount for enkephalinase B inhibition of a compound having the formula:

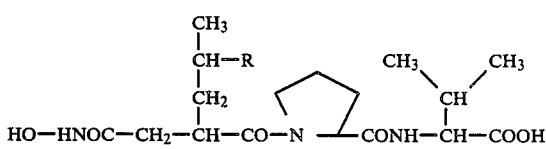

wherein R represents a hydrogen atom or a methyl group, or a pharmaceutically acceptable salt thereof, together with a pharmaceutically acceptable carrier.

* * * * *